United States Patent [19]

Cutchens et al.

[11] 4,429,159

[45] Jan. 31, 1984

[54] CATALYST SEPARATION IN PRODUCTION OF AMINES

[75] Inventors: Charles E. Cutchens, Pensacola, Fla.; Lynn H. Lanier, Decatur, Ala.

[73] Assignee: Monsanto Company, St. Louis, Mo.

[21] Appl. No.: 476,741

[22] Filed: Mar. 18, 1983

[51] Int. Cl.$^3$ .................. C07C 87/14; C07C 87/16
[52] U.S. Cl. ............................ 564/492; 564/490; 564/491
[58] Field of Search .................. 564/492, 490, 491

[56] References Cited

U.S. PATENT DOCUMENTS

| | | | |
|---|---|---|---|
| 3,821,305 | 6/1974 | Bartalini | 260/584 K |
| 4,053,516 | 10/1977 | Hammerstrom et al. | 260/585 A |
| 4,359,585 | 11/1982 | Campbell et al. | 564/492 |
| 4,395,573 | 7/1983 | Cutchens et al. | 564/492 |

OTHER PUBLICATIONS

U.S. Patent Applications: Ser. No. 369,443, filed Apr. 19, 1982, titled: "Improved Production and Separation of Amines", Charles E. Cutchens et al., inventors.

*Primary Examiner*—Paul F. Shaver
*Attorney, Agent, or Firm*—Thomas Y. Awalt, Jr.

[57] ABSTRACT

In the production of amines from nitriles where the nitriles are hydrogenated under pressure in the presence of a Raney Nickel Catalyst using hydrogen produced from methane and containing $CO_2$, a more efficient separation of the product hexamethylene diamine from the catalyst is obtained by maintaining a specified carbonate concentration. This specific carbonate concentration improves the settling characteristics of the catalyst and reduces catalyst carryover into the crude hexamethylene diamine during decantation.

6 Claims, 1 Drawing Figure

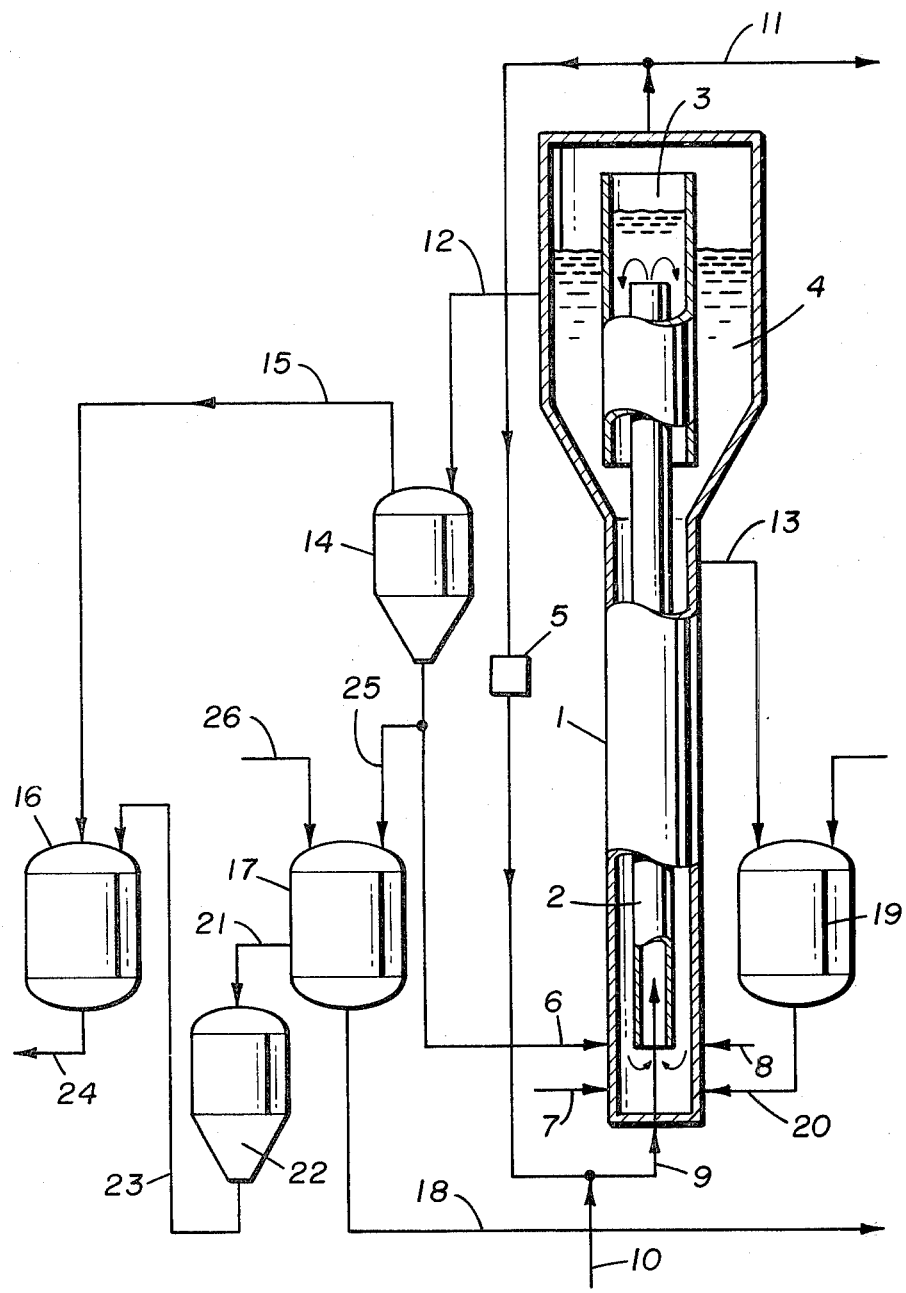

CATALYST SEPARATION IN PRODUCTION OF AMINES

A. FIELD OF THE INVENTION

The invention relates to a process for the production of an amine such as hexamethylene diamine from a nitrile such as adiponitrile where the nitrile is hydrogenated under pressure in the presence of a Raney Nickel catalyst, the reaction being conducted in a reactor from which is discharged a product stream containing both the amine and Raney Nickel catalyst.

B. BACKGROUND OF THE INVENTION

It is well known that amines such as hexamethylene diamine can be produced by the catalytic hydrogenation of nitriles such as adiponitrile in the presence of Raney Nickel catalysts.

One such process is described in U.S. Pat. No. 3,821,305, in which hydrogenation is conducted in liquid phase at pressures of from 20-50 atmospheres and temperatures of 60°-100° C. in the presence of finely divided Raney Nickel catalyst and an inorganic base. Hydrogen and adiponitrile are fed into a liquid reaction medium consisting of hexamethylene diamine, water, the inorganic base, and the catalyst, in which medium the content of base is maintained in the range of 0.2-12 moles per kilogram of catalyst, while the content of water is maintained in the range of 2-130 moles per mole of the base.

The process discharge stream in the above described process contains both Raney catalyst and the product hexamethylene diamine, from which it is desirable to recover substantially pure hexamethylene diamine by distillation, and to recycle the Raney Nickel catalyst.

Before distillation of the process discharge stream, the stream is ordinarily fed to a decanter or container from which the crude hexamethylene diamine is removed as an upper layer and a catalyst slurry is removed as the lower layer. This catalyst slurry is normally washed so as to remove foreign materials including aluminates, carbonates and caustic. This washing, through recycling of the catalyst slurry, increases the settling rate of the catalyst in the decanter.

However, separation in the decanter has been found to be inefficient due to a high content of fines in the upper (product) layer.

Any method whereby the setting characteristics of the product stream could be substantially improved would constitute a significant advance in the art and in an object of this invention.

SUMMARY OF THE INVENTION

Briefly, the invention is an improvement in the process for the production of amines (such as hexamethylene diamine) from nitriles (such as adiponitrile) where the nitrile is hydrogenated using hydrogen produced from methane and containing $CO_2$; and where the hydrogenation is conducted under pressure in the presence of a Raney Nickel catalyst continuously in a reactor to produce the amine; and where the amine is discharged into a stream from which is recovered by separation a crude amine stream being the upper layer and a catalyst slurry stream being the lower layer; and where the catalyst slurry stream is washed to remove aluminates, carbonates and caustic so as to increase the settling rate of the catalyst in the decanter. I have discovered that although the settling rate of catalyst in the decanter is increased by washing and thus essentially removing aluminates and carbonates, the same washing also results in an increase in the amount of fines in the upper layer, which fines can be reduced, with a substantial consequential improvement of the settling characteristics of the catalyst in the decanter, by reducing the wash to such a rate and by maintaining such a rate as to result in an essentially constant carbonate concentration (measured as $CO_2$) of 0.12-0.4 percent, preferably 0.2-0.25 percent. By "essentially constant" is meant within a range of about 0.3%.

In the detailed description, reference will be made to the drawing in which the FIGURE is a flow sheet showing the wash system of a hexamethylene diamine reaction.

DETAILED DESCRIPTION OF THE INVENTION

While the invention is applicable to any process for the production of an amine from a nitrile in which a Raney Nickel catalyst is employed, the invention will be described in the context of a preferred process for such production.

The process for the production of hexamethylene diamine (HMD) is preferably carried out in pressures of 20-50 atmospheres in temperatures of 60°-100° C., by feeding molecular hydrogen and adiponitrile into a liquid reaction medium containing, along with the hexamethylene diamine produced, water, sodium hydroxide and a finely divided Raney Nickel catalyst dispersed in the liquid components of the reaction medium. The catalyst, which may be Raney Nickel, or Raney Nickel containing small amounts of other metals such as chromium, loses all or most of its activity during hydrogenation. In order to maintain a given level of catalytic activity within the catalytic mass, it is necessary for the catalyst in the reaction medium to be gradually replaced. This replacement is effected by feeding fresh catalyst to the reaction vessel and removing a quantity of reaction medium which contains an amount of catalyst equal to that supplied. The fed catalyst may consist of a mixture of fresh catalyst and of recycled catalyst. Recycled catalyst is catalyst that has been washed prior to re-use.

The reaction medium preferably contains:
(1) a quantity of catalyst in excess of 1 part, by weight, per 100 parts of liquid reaction medium (hexamethylene diamine, water and sodium hydroxide), the upper limit depending solely on the fluidity of the reaction medium; the preferred range being from 3 to 35 parts per 100 parts by weight of the liquid reaction medium;
(2) a quantity of sodium hydroxide in the range of 0.2 to 12 gm moles per kilogram of catalyst and preferably between 0.5 and 2 gm moles per kilogram of catalyst;
(3) a quantity of water in the range of 2 to 130 moles per mole of sodium hydroxide and preferably between 4 and 40 moles per mole of sodium hydroxide.

Substantially similar results in the production of the amine can be obtained by using, instead of sodium hydroxide, a hydroxide of any other of the alkali metals. Throughout the following description, however, reference will be made to the preferred sodium hydroxide.

The liquid part of the reaction medium, under the starting conditions already specified, and within the preferred range of ratio of water to sodium hydroxide, consists of two phases. One phase, amounting to 0.5–5.0 parts per 100 parts of the other phase, consists of an aqueous solution of sodium hydroxide whose concentration is in the range of 25 to 55 percent by weight. The other phase consists of hexamethylene diamine containing water and small amounts of sodium hydroxide. The aqueous solution of sodium hydroxide, which is the heavier phase, contains most of the catalyst.

The equipment for continuous operation of the process is of conventional type. An example of this, which is not limitative of the invention, is shown in the accompanying drawing. The equipment consists essentially of a vertical tubular reaction vessel, 1, provided inside with an injection device, 2, such as to promote the agitation of the reaction medium resulting from the hydrogen flow, and at the top with containers, 3 and 4, which enable the separation of the gas from the liquid and the drawing off from the reaction vessel of a hydrogenated product having a low content of catalyst thus making it possible to maintain in the reaction vessel relatively high concentrations of catalyst—for example, 10 to 30 parts of catalyst per 100 parts by weight of liquid reaction medium.

The equipment also includes a gas re-cycling pump, 5, and pipes for feeding the reaction vessel with adiponitrile solution of sodium hydroxide, 8, and hydrogen, 9. The hydrogen consumed is replaced by feeding fresh hydrogen through pipe 10.

Part of the gas is vented through pipe 11, the purpose of this release being to maintain the hydrogen content in the re-cycled gas above a given value.

Product stream 12 from the reactor is discharged into decanter 14 where the upper layer containing crude hexamethylene diamine is discharged through pipe 15 and on to settling tank 16, thence through pipe 24 to further purification measures including distillation. The lower layer of the decanter, 14, is separated into two portions, the first going to pipe 6 which is returned to the reactor and the second going to pipe 25 which discharges into wash tank 17. Wash tank 17 is fed by pipe 26 containing water, and the washed catalyst is returned to the reactor via catalyst tank 19 and pipe 20. The catalyst wash water is discharged from tank 17 into hold tank 22 via pipe 21, thence through pipe 23 to pipe 16.

According to this invention, the washing in tank 17 is controlled and limited to provide a resulting carbonate concentration of 0.12–0.4 weight percent measured as carbon dioxide, with a preferred weight percent range of 0.2–0.25. Within these ranges I have discovered the settling characteristics of the catalyst in the decanter are surprisingly and substantially improved due to a substantial decrease in the amount of fines in the upper layer; and this improvement in turn results in a minimum of catalyst carryover into the crude hexamethylene diamine stream through pipe 15. The reduction of the fines in the upper layer can be seen as a clear upper phase.

While the above may appear to suggest that washing can be omitted entirely, this is not the case. Washing is still required to eliminate certain impurities and a buildup of those already noted beyond a workable limit. It is also important to note that while minimizing reduction of aluminates and carbonates, as has been previously pointed out, the settling rate in the decanter is reduced. Should the reduction extend beyond any upward flow velocity in the decanter, the purpose of this improvement will have been defeated, and catalyst carryover into the crude hexamethylene diamine will result. In at least one system it has been found desirable to operate the catalyst wash rate so as to maintaining the settling rate between one and two inches per minute, the catalyst bulk volume in the decanter at 50–60 percent, using enough wash water to keep the caustic/$H_2O$ ratio in the catalyst wash water below 0.006 before returning it to the crude hexamethylene diamine product stream.

In the examples, "settling rate" was determined as follows: A sample of the reactor underflow is added to a 500 ml graduated cylinder so that there is about 200 ml of settled catalyst. The temperature is brought to 90° C. and the catalyst is allowed to settle for 30 minutes. The volume of the catalyst and total volume of the slurry is measured. HMD from the decanter 14 overflow is added to bring the total volume to 500 ml. The sample is shaken and the time in which the catalyst layer settles 3 inches is measured. The settling time is repeated 3 times. The bulk volume is the ratio of the catalyst settled volume to the original total volume of the slurry. The settling rate is three inches divided by the average of the three settling times, expressed in inches per minute.

COMPARATIVE EXAMPLE I

The diamine reactor shown in the drawing was run with 180,000 lbs of reaction slurry of which 45,000 lbs was Raney Nickel catalyst. Periodically, a portion, (typically 10,000 lbs) of decanter underflow material, was drained from decanter 14 through pipe 25 to catalyst regeneration tank 17. This material had a catalyst concentration of about 35 percent, containing about 3,500 lbs of catalyst. One thousand gallons of water was added to the catalyst mixture, and the slurry was agitated, settled, and the liquid phase was drained to wash water tank 22 through pipe 21. The wash was respected with 700 gallons and then 500 gallons of water. On the last wash regeneration step hydrogen was bubbled through the mixture prior to settling and decanting. The wash water was mixed in tank 16 with crude HMD which was fed thereto through pipe 15, and the washed catalyst was slurried with hexamethylene diamine and pumped back into the reactor through pipe 18, catalyst slurry tank 19 and pipe 20. According to this process, over a period of time, employing wash rates of 7–15 weight units of catalyst per thousand weight units of adiponitrile, the equilibrium level of aluminates, carbonates and caustic were low enough so that the settling rate of the catalyst in decanter 14 was rapid, but the upper layer in the decanter was cloudy, the cloud resulting in a visible amount of fines (including minute particles of Raney Nickel catalyst), and this resulted in a relatively constant catalyst carryover of an average of about 40 ppm or higher.

COMPARATIVE EXAMPLE II

This operation of the reactor was conducted as described above, except that the catalyst was not washed. The major effect noted was a high sodium content in the diamine reactor, settling rates in the decanter of about 0.2–0.8 and while catalyst carryover during a four month period was low, a buildup in the level of carbonate and hydroxides gave rise to a massive carryover shortly after re-establishing moderate levels of washing.

EXAMPLE III

Employing the same general reaction, but lowering the wash rate in this system from about 7–15 weight units of catalyst per thousand weight units of adiponitrile to about 3–5 weight units of catalyst per thousand weight units of adiponitrile, the settling rate increased although not as high as in Example I, reaching 3–5 inches per minute, and except for one minor catalyst carryover when the carbonate concentration was at a level of about 0.6, catalyst carryover was held to an average of about 35 ppm.

Of course, other factors may influence catalyst carryover. For example, the caustic content is considered most important in this respect, but caustic content can be controlled without regard to catalyst wash procedures. Also considered important is the concentration of aluminates which are inherent in the Raney Nickel catalyst hydrogenation, but whose concentration follows generally that of the carbonate concentration. As indicated above, the concentration of water in the decanter is also a factor, and the preferred concentration of water has been given above.

We claim:

1. In a process for the production of an amine from a nitrile where the nitrile is hydrogenated, using hydrogen produced from methane and containing carbon dioxide, under pressure in the presence of a Raney Nickel catalyst continuously in a reactor thereby to produce the amine which is discharged into the stream from which is recovered by separation in a vessel a crude amine stream from the upper layer and a catalyst slurry stream from the lower layer, the improvement comprising maintaining an essentially constant carbonate concentration at such a level during separation as to minimize the amount of fines in the upper layer, improve settling characteristics of the catalyst in the vessel and reduce consequent catalyst carryover into the crude amine stream.

2. The process improvement of claim 1 wherein the resulting concentration of the carbonate in the decanter measured in the form of carbon dioxide is 0.2–0.25 percent.

3. The process improvement of claim 1 wherein the ratio of sodium hydroxide to water in the catalyst wash water is less than 0.006.

4. In a process for the production of hexamethylene diamine from adiponitrile where the adiponitrile is hydrogenated, using hydrogen produced from methane and containing $CO_2$, under pressure in the presence of a Raney Nickel catalyst continuously in a reactor thereby to produce hexamethylene diamine which is discharged into a stream from which is recovered by separation in a container a crude hexamethylene diamine stream being the upper layer and a catalyst slurry stream being the lower layer, and where the catalyst slurry stream is washed to remove aluminates and carbonates, and to increase the settling rate of the catalyst in the decanter, incidentally increasing the amount of fines in the upper layer, and where the washed catalyst is recycled to the reactor, the improvement comprising maintaining the wash at such a rate as to result in a carbonate concentration measured as $CO_2$ of 0.12–0.4 percent thereby to decrease the amount of fines in the upper layer, improve settling characteristics of the catalyst in the decanter and reduce consequent catalyst carryover into the crude hexamethylene diamine stream.

5. The process improvement of claim 4 wherein the resulting concentration of the carbonate in the decanter, measured in the form of carbon dioxide is 0.2–0.25 percent.

6. The process improvement of claim 4 wherein the ratio of sodium hydroxide to water in the catalyst wash water is less than 0.006.

* * * * *